United States Patent [19]

Kruger et al.

[11] Patent Number: 4,577,222
[45] Date of Patent: Mar. 18, 1986

[54] APPARATUS AND METHOD FOR CROSS SECTIONAL IMAGING OF A BODY

[75] Inventors: Robert A. Kruger, Sandy; James A. Nelson, Salt Lake City, both of Utah

[73] Assignee: Thomson-CSF Broadcast, Inc., Stamford, Conn.

[21] Appl. No.: 444,613

[22] Filed: Nov. 26, 1982

[51] Int. Cl.$^4$ .............................................. H04N 5/32
[52] U.S. Cl. ..................................... 358/111; 378/99; 378/4
[58] Field of Search .................... 358/111; 378/99, 4, 378/5, 8; 128/653, 654, 691; 364/414, 416

[56] References Cited

U.S. PATENT DOCUMENTS

| | | | |
|---|---|---|---|
| 4,071,769 | 1/1978 | Brunnett et al. | 378/4 |
| 4,291,333 | 9/1981 | Warnock et al. | 358/36 |
| 4,298,799 | 11/1981 | Oliver | 378/4 |
| 4,437,161 | 3/1984 | Anderson | 358/111 |

*Primary Examiner*—Edward L. Coles, Sr.
*Attorney, Agent, or Firm*—Martin Novack

[57] ABSTRACT

The disclosure is directed to a method and apparatus for generating a processed image of a cross-section through a body. Fluoroscopic tomography is achieved wherein a series of video frames of a cross-section of a body can be viewed in real time. In this manner, for example, one can monitor the progress of a bolus of contrast material moving through a blood vessel in the cross-section being viewed. In a form of the disclosure, a recorded series of frames of a principal plane of a body being imaged can be processed to obtain a corresponding series of frames that represent a plane of interest that is spaced from the principal plane, thereby avoiding the necessity of re-exposure for each new plane to be viewed. In accordance with the disclosed method, a body is disposed between a combination of a source of radiation and an associated detector, such that a beam of radiation from the source impinges angularly on the body and passes through to the detector. Relative rotational motion is effected between the beam and the body, such that a principal plane of interest in the body remains substantially in focus during the relative rotational motion. A series of frames of electronic video signals are derived from the detector, at different rotational positions, the frames representing images of the radiation transmission characteristics of the body at a series of successive times. The series of frames are temporally filtered and then displayed. In a preferred embodiment, the temporal filtering step comprises filtering the series of frames of video signals with a filter function having a temporal frequency response that corresponds substantially the temporal frequency of the movement of a bolus of contrast material through the region being imaged.

22 Claims, 12 Drawing Figures

APPARATUS AND METHOD FOR CROSS SECTIONAL IMAGING OF A BODY

BACKGROUND OF THE INVENTION

This invention relates to imaging of the internal structure of a body and, more particularly, to an apparatus and method for obtaining images of cross-sections through a body.

In conventional tomography, the objective is typically to obtain an image of one or more cross-sections or planes of the internal structure of a body by combining information from a number of images obtained at different rotational perspectives to obtain a single processed image for each cross-section. Typically, the multiple images are processed and added by computer or photographically to obtain an ultimately processed single image. The procedure can then be repeated for other cross-sections or planes within the body.

It is known that a series of fluoroscopic images can be viewed to visualize the progress of a bolus of contrast material through a blood vessel of interest. Radiographic contrast agents are used to create a large difference in x-ray absorption behavior where little or none previously existed. Blood vessels are virtually invisible on fluoroscopic images (except in the chest) becuase blood, muscle, fat and soft tissue all possess similar x-ray absortpion behavior. Radiographic contrast agents contain material which has x-ray absorption properties dissimilar to blood, muscle, fat and the soft tissue. For example, when a bolus of iodinated liquid contrast material is injected into an artery or vein, the vascular structure is given artificially higher contrast on an x-ray image while the contrast material is present within a certain vascular segment.

Recently, various techniques have been developed for processing fluoroscopic images, such as with temporal filters to obtain improved images. However even these improved images can have limited usefulness in certain applications, such as where confusing overlying vasculature or other anatomy restricts the view. In such cases a cross sectional view is often necessary or desirable.

It is among the objects of the present invention to provide images of body cross-sections by a type of fluoroscopic tomography which presents, in real time, a sequence of video frames representative of a body plane of interest. It is also among the objects of the present invention to provide an apparatus and technique whereby sequences of processed images representative of different planes of interest in the body can be presented, without the need for submitting a patient to a new sequence of exposures for each plane to be presented. It is also among the objects of the present invention to employ fluoroscopic imaging and processing techniques in a tomographic type of system to obtain advantages over existing tomographic and fluoroscopic techniques.

SUMMARY OF THE INVENTION

The present invention is directed to a method and apparatus for generating a processed image of a cross-section through a body. In the present invention, fluoroscopic tomography is achieved wherein a series of video frames of a cross-section of a body can be viewed in real time. In this manner, for example, one can monitor the progress of a bolus of contrast material moving through a blood vessel in the cross-section being viewed. In a form of the invention, a recorded series of frames of a principal plane of a body being imaged can be processed to obtain a corresponding series of frames that represent a plane of interest that is spaced from the principal plane, thereby avoiding the necessity of re-exposure for each new plane to be viewed.

In accordance with the method of the invention, a body is disposed between a combination of a source of radiation and an associated detector, such that a beam of radiation from the source impinges angularly on the body and passes through to the detector. Relative rotational motion is effected between the beam and the body (e.g., by moving the source/detector combination, the body, or both) such that a principal plane of interest in the body remains substantially in focus during the relative rotational motion. A series of frames of electronic video signals are derived from the detector, at different rotational positions, the frames representing images of the radiation transmission characteristics of the body at a series of successive times. The series of frames are temporally filtered and then displayed.

In the preferred embodiment of the invention, the temporal filtering step comprises filtering the series of frames of video signals with a filter function having a temporal frequency response that corresponds substantially the temporal frequency of the movement of a bolus of contrast material through the region being imaged. Preferably, this temporal response becomes very small at a time that is less than the characteristic rotational time of the tomography system. In this manner, the temporal filter operates to filter out the tomography motion, as well as certain other types of motion and, if desired, stationary anatomy.

In a form of the invention, each frame of the derived series of frames includes an array of pixels, the video signal level at each pixel being determined by the radiation transmissivity of an elemental region of the principal plane and adjacent planes through which the rays of the beam pass. In order to image a plane of interest other than the principal in-focus plane, geometrical transformations are implemented to shift the video signal levels to different pixel positions, the transformations being a function of the relative rotational angle associated with the frame containing the pixel, and the distance between the plane of interest to be imaged and the principal plane.

Further features and advantages of the invention will become more readily apparent from the following detailed description when taken in conjunction with the accompanying drawings.

DESCRIPTION OF THE PREFERRED EMBODIMENT

Figure 1:
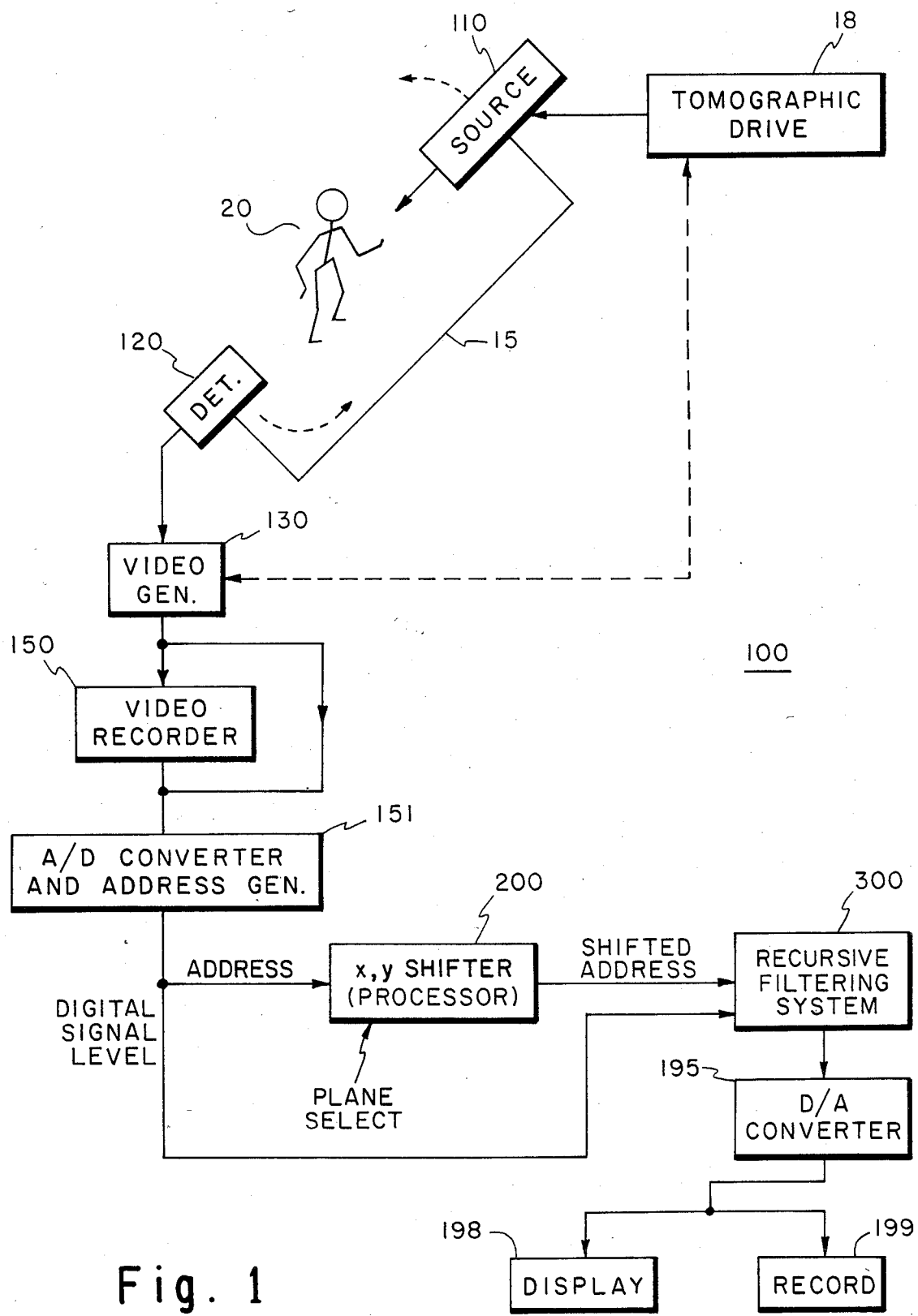
FIG. 1 is a block diagram of an apparatus in accordance with the invention, and which can be used to practice the method of the invention.

Referring to FIG. 1 there is shown a block diagram of an embodiment of an apparatus 100 for obtaining cross-sectional images of the internal structure of a body 20. The apparatus 100 includes a conventional circular or elliptical tomography mechanism 15 modified for fluoroscopic application. A radiation source 110, typically an x-ray source, and a detector 120 are mounted to rotate in coordinated fashion, e.g. around an axis of the body 20, under control of a tomographic drive 18. The tomography mechanism may be of the type manufactured by CGR Medical Corp. of Baltimore, Md. A video generator 130 operates in conjunction with the detector 120. The combination of detector and video generator may include, for example, an x-ray image intensifier in conjunction with a television camera. The output of video generator 130 is coupled to video recorder 150, and also to an analog-to-digital converter 151 which converts the television signal into digital form and generates sequential addresses. The output of recorder 150 is also coupled to the converter 151. Equipment for obtaining the digitized television signal is well known in the art and commercially available, an example being the model AD-964310 manufactured by Thomson-CSF Broadcast, Inc. At each pixel of the video frame, the television signal digitizer generates a digital signal, such as an eight bit digital signal, representative of one of 256 gradations of luminance level (for a monochrome signal—as considered in the present illustrated embodiment), along with an address which defines the pixel position. The video recorder 150 may be any suitable recording device such as a video tape recorder or disc recorder. The video generator, the video recorder, and the analog-to-digital converter conventionally receive synchronizing signals, and the analog-to-digital converter also receives clock signals at the pixel rate.

Figure 11:
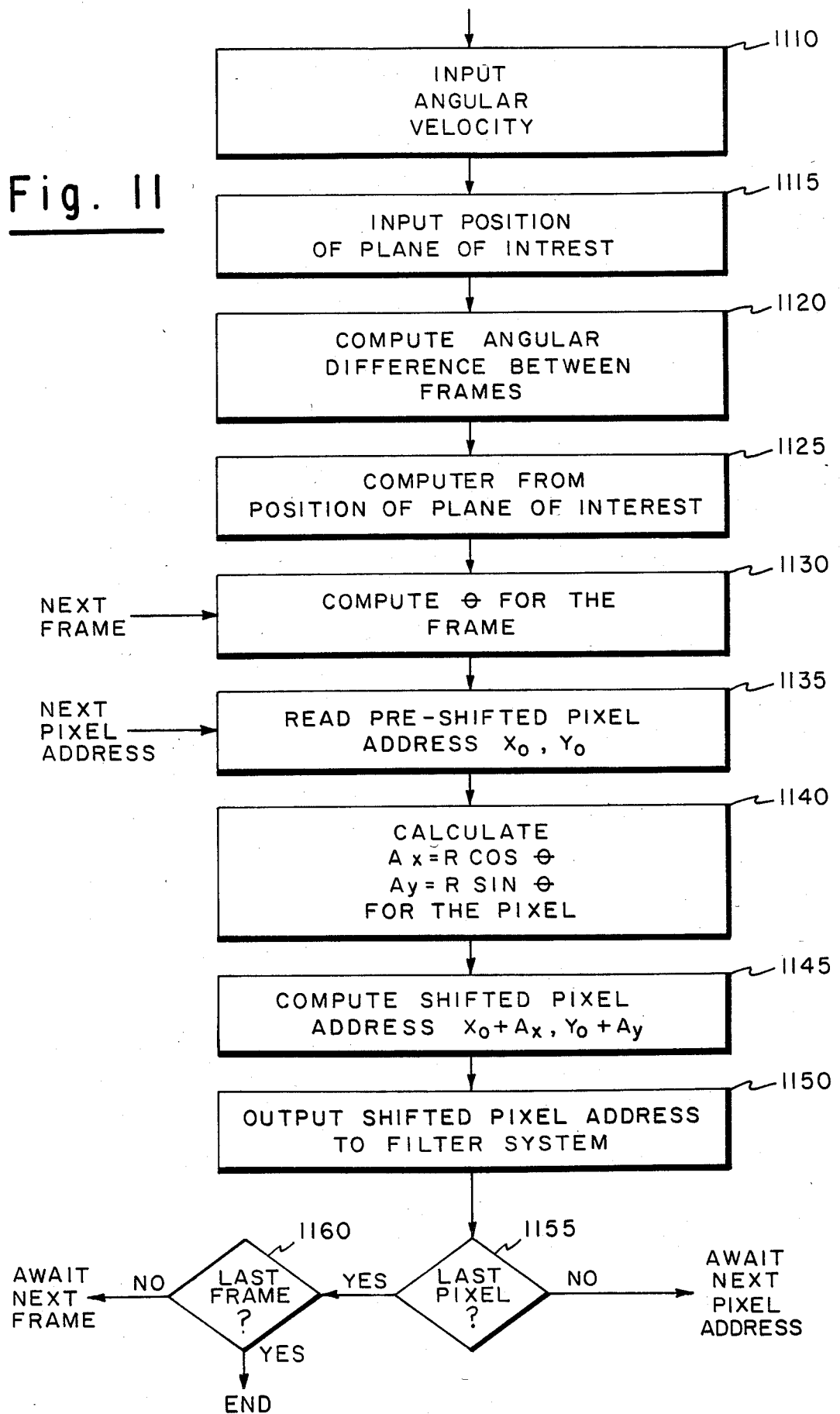
FIG. 11 shows a flow diagram of a routine for controlling the processor of the FIG. 1 embodiment to implement shifting of pixel addresses to observe a plane of interest other than the principal plane.

The output of the analog-to-digital converter 151 is coupled to x, y shifter circuitry 200 which may comprise a processor such as a general purpose digital computer or microprocessor. The processor 200, may comprise for example a model 68000 microprocessor manufactured by Motorola Corp., or a so-called "bit slice" implementation thereof. The processor, which may be programmed in accordance with the routine described in conjunction with FIG. 11, is operative to shift the address of a current pixel, the shifted pixel address being coupled to the recursive filtering system 300. The digital signal level for the current pixel is also coupled to the recursive filtering subsystem 300, which is described in conjunction with FIG. 12. The output of recursive filtering system 300 is coupled to a digital-to-analog converter 195 whose output is coupled to display 198 and to a video recorder 199. Again, it is assumed that sync signals and clock signals, are conventionally available to these circuits.

Before further description of the operation of the system, some theoretical considerations will be set forth.

Figure 2:
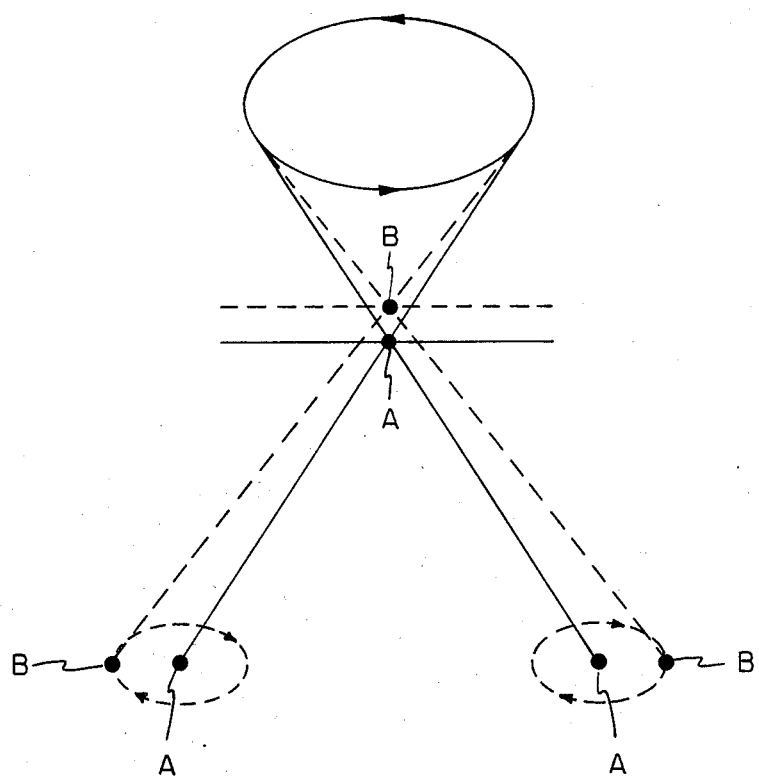
FIG. 2 is a simplified diagram of rays of the radiation beam which is useful in understanding operation of a feature of an embodiment of the invention.

Consider a circular tomographic motion where, as in the present case, the film plane has been replaced by an image intensifier-television chain. Assume that the circular motion repeats at a rate such as once per second. The tomographic angle is unspecified. FIG. 2 shows the geometry and the position of two points in a 3-D object to be imaged, one in the principal (or infocus) plane, and a second in a plane above. [Because the image intensifier input surface is not flat, infocus planes are really two dimensional curved surfaces, similar in shape to the image intensifier input surface. Since the curvature is small this distortion is not considered of any great consequence.] Assume for the moment that the 3-D object is stationary.

The projection of the infocus point always falls on the same pixel (same point on image intensifier surface). The projection of the point in the plane above traces out a circle on the image intensifier surface. The farther removed an out-of-focus plane is from the infocus plane, the greater will be the diameter of this circle. A single pixel lying along the trajectory of this point on the image intensifier surface "sees" this point once per second. The temporal image variations associated with these two points ar shown in FIGS. 3 and 4, respectively.

Figure 4:
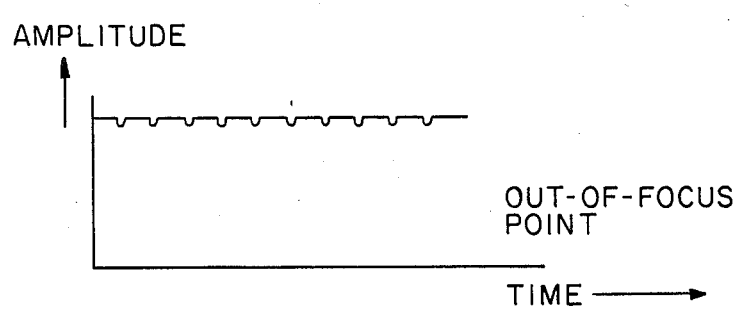
FIG. 4 is a graph which illustrates the temporal variation associated with an out-of-focus point.
Figure 5:
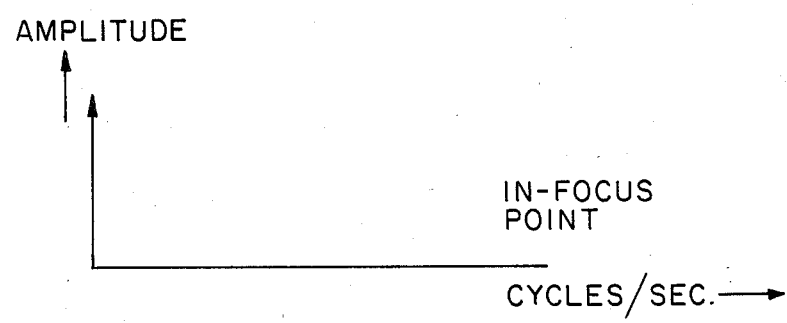
FIG. 5 is a graph which illustrates the temporal frequencies associated with an in-focus point.
Figure 6:
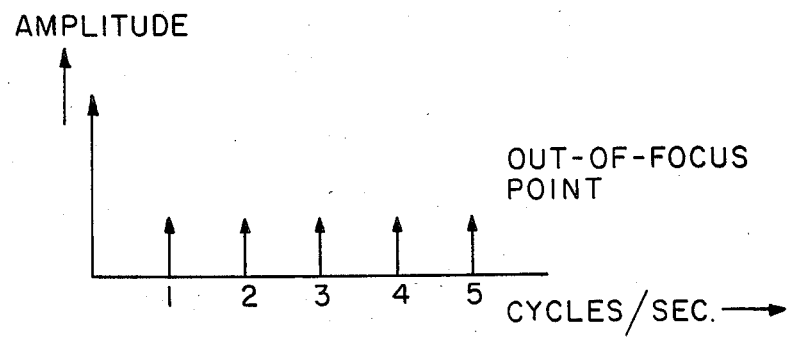
FIG. 6 is a graph which illustrates the temporal frequencies associated with an out-of-focus point.

Now, rather than looking at the temporal variations of the projections of these points, consider the temporal frequency components associated with these variations. These are shown in FIGS. 5 and 6 and represent the Fourier Transforms of FIGS. 3 and 4, respectively. The infocus point contributes only a d.c. component at zero temporal frequency. The out-of-focus point contributes a d.c. component, and also spikes at ±1 cycle/sec and all the higher harmonics at ±n cycles/sec, where n is an integer.

Figure 7:
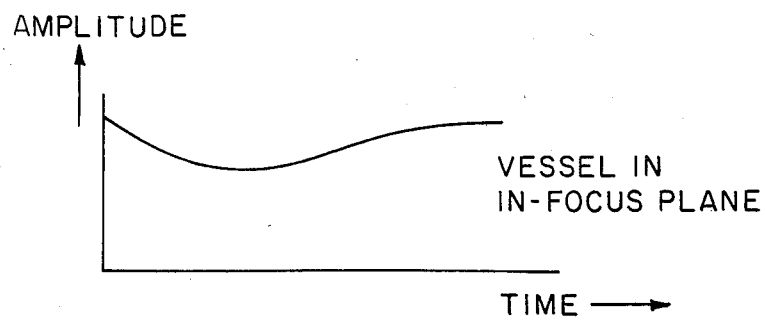
FIG. 7 is a graph which illustrates the temporal variation associated with a vessel in an in-focus plane.
Figure 8:
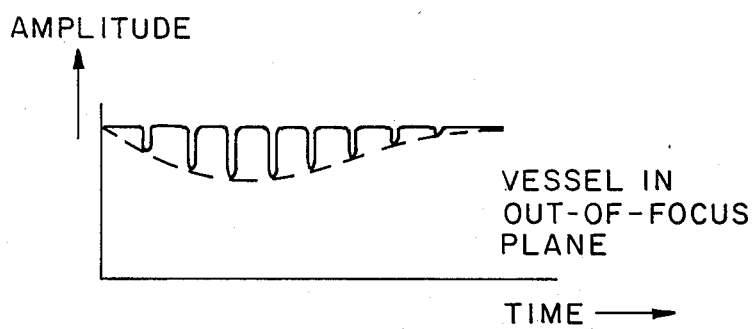
FIG. 8 is a graph which illustrates the temporal variation associated with a vessel in an out-of-focus plane.
Figure 9:
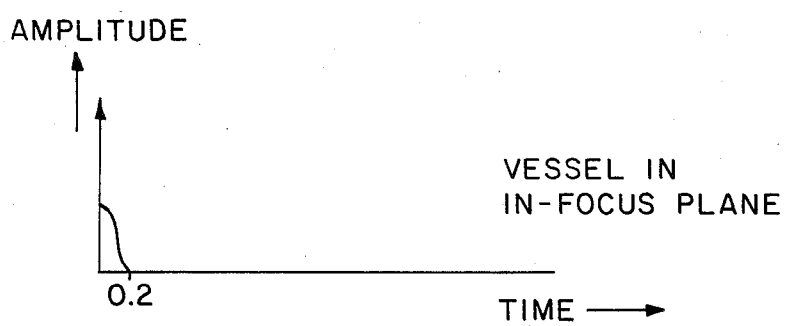
FIG. 9 is a graph which illustrates the temporal frequencies associated with a vessel in an in-focus plane.
Figure 10:
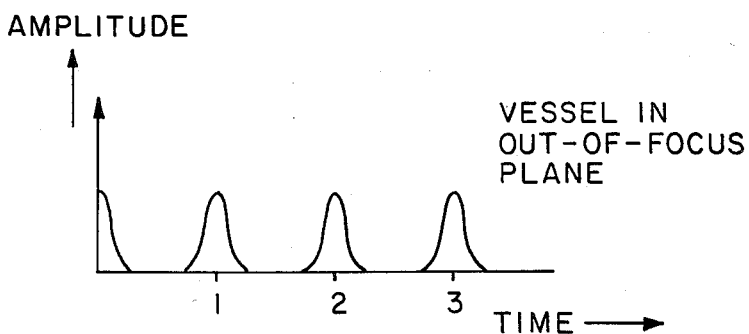
FIG. 10 is a graph which illustrates the temporal frequencies associated with a vessel in an out-of-focus plane.

Now assume that rather than a stationary object, two arteries are present carrying opacified blood due to an I.V. injection of contrast material. One vessel passes through point A, the other through point B. The temporal image variations shown in FIGS. 3 and 4 can now be considered as being modified to those shown in FIGS. 7 and 8. The temporal frequency components associated with these variations are shown in FIGS. 9 and 10, respectively.

Figure 12:
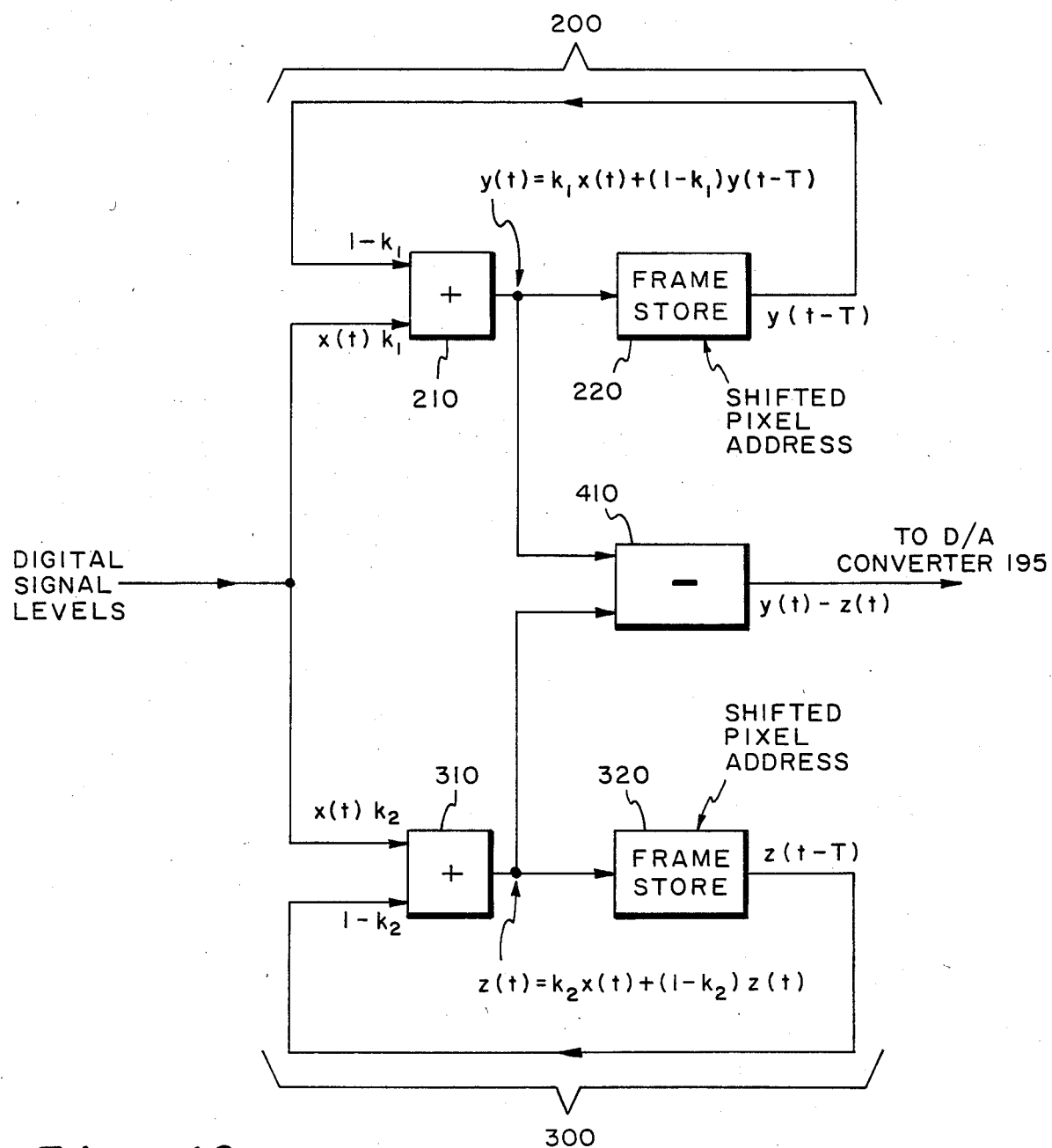
FIG. 12 is a block diagram of a temporal filtering system which can be utilized in the FIG. 1 embodiment.

Most of the temporal frequency components can be eliminated from out-of-focus planes, while at the same time removing stationary background anatomy from all planes, by passing the video signals from the tomographic sequence through a recursive filtering system, such as the filtering system illustrated in FIG. 12, and described in the copending U.S. application Ser. No. 342,376, filed Jan. 25, 1982, assigned to the same assignee as the present application. The filter response at zero temporal frequency is near zero, and above 1 Hz. it is very small. The combined effect of rapid periodic motion and bandpass filtration is to eliminate most nonarterial structures and visualize arteries within a region of the in-focus plane with good resolution and to image arteries from further removed planes as blurry arteries, the blur increasing with distance from the infocus plane. Other temporal filters can be employed. Also, the in-focus plane can be changed by moving the patient or stepping the tomography mechanism.

A limitation to the described imaging approach is that although it can be implemented in real-time, only one plane is imaged. However, as noted above, if the original image sequence is stored, one can use this sequence in such a way as to synthesize other planes without reexposing the patient. During the original data acquisition process projections of points in out-of-focus planes trace out circular trajectories in the detector plane. By keeping track of the angular position associated with each digitized video frame, one can determine the image shifts (angle and radius) associated with any given plane for any specified angular position. In order to reconstruct dynamic sequences depicting flow through other than the original infocus plane one can compensate for such shifts on a frame-by-frame basis, in effect tracking a preselected trajectory characteristic of a particular plane. This is accomplished in the present embodiment by offsetting the digital (x,y) addressing in compensation for the predetermined shifts.

Figure 3:
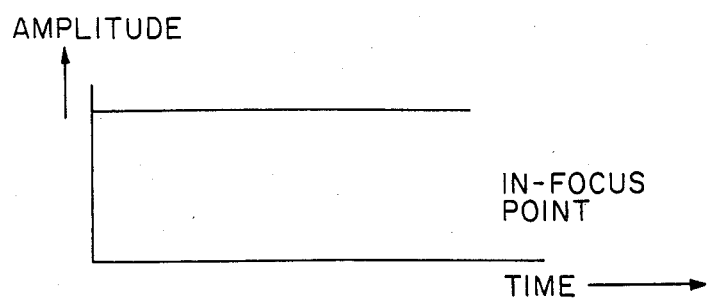
FIG. 3 is a graph which illustrates the temporal variation associated with an in-focus point.

In FIG. 3, if the radius of the circle associated with the point B is R (which is a geometrically known function of the distance between points A and B, and the tomographic angle, $\phi$), and the rotation angle, with respect to a reference, is $\theta$, then the x and y displacements of the point, designated $\Delta x$ and $\Delta y$, respectively, can be represented as:

$$\Delta x \times R \cos \theta \tag{1}$$

$$\Delta y = R \sin \theta \tag{2}$$

If the original unshifted coordinates of the point were $x_o$, $y_o$, then the shifted coordinates $x'$, $y'$ would be $$x' = x_o - \Delta x \tag{3}$$

$$y' = y_o - \Delta y \tag{4}$$

FIG. 11 is a flow diagram of the routine for controlling processor 200 (FIG. 1) to implement the shifting of pixel addresses to observe a plane of interest other than the principal plane. The angular velocity of the tomography system is input (block 1110), and the position of the plane of interest, i.e., its distance and direction from the principal plane, is also input (block 1115). The angular difference between frames is then routinely obtained from the input angular velocity and the number of frames per second to be used, this function being represented by the block 1120. The basic radius, R, is then determined as a function of the plane of interest and the tomographic angle (block 1125). The characteristic angle, $\theta$, is then computed for the next arriving frame, by adding the angular difference between frames to the current accumulation of angles (block 1130). When the next pixel address of the frame arrives, the pre-shifted pixel address, $x_o$, $y_o$ is read (block 1135). Relationships (1) and (2) are then utilized to calculate the shift components $\Delta x$ and $\Delta y$, as represented by the block 1140. The shifted pixel address, $x_o + \Delta x$ and $y_o + \Delta y$, is then computed, as represented by the block 1145. The shifted pixel address is then output to the filter system (block 1150), and a determination is made as to whether or not the pixel whose address was just processed was the last visible pixel of a frame (diamond 1155). If not, the next pixel is awaited, whereupon block 1135 is re-entered. When the last pixel has been processed, a determination is made (diamond 1160) as to whether or not the last frame of the sequence has been processed. If not, the next frame is awaited, whereupon block 1130 is reentered. When the last frame has been processed, the routine is terminated.

Referring to FIG. 12, there is shown a block diagram of a temporal filtering system 300 which, in the present embodiment, is of the type disclosed in the aboveferenced copending U.S. application Ser. No. 342,376, filed Jan. 25, 1982, assigned to the same assignee as the present application. The temporal filtering system includes a first recursive filtering subsystem 200 and a second recursive filtering subsystem 300. The subsystem 200 includes an adding circuit 210 that receives, at one input thereof, the signal that is output from analog-to-digital converter 151, and is designated x(t), and receives, at its other input, a signal designated y(t−T), to be described, where T is the video frame period. The input of adding circuit 210 which receives the signal x(t) is weighted by a weighting factor $k_1$, and the input of adding circuit 210 which receives the signal y(t−T) is weighted by a weighting factor $(1-k_1)$. The output of adding circuit 210 is a signal designated y(t), and this signal is coupled to a digital frame store 220. The digital frame store may comprise, for example, a model FS-963155 digital video frame store manufactured by Thomson-CSF Broadcast, Inc. or, alternatively, may be any suitable memory, such as a random access memory, having pixel addresses (if unshifted) derived by the address generator portion of block 151 sync and clock signals. When shifted addresses are used to view planes other than the principal plane, these are input from processor 200, as described above. The output of the digital frame store 200, in this embodiment, is the signal designated y(t), i.e., the output of the adding circuit 210.

The second recursive filtering subsystem 300 includes an adding circuit 310 that receives, at one input thereof, the signal that is output from analog-to-digital converter 151, and is designated x(t), and receives, at its other input a signal designated z(t−T), to be described. The input of adding circuit 310 which receives the signal x(t) is weighted by a weighting factor $k_2$, and the input of adding circuit 310 which receives the signal z(t−T) is weighted by a weighting factor $(1-k_2)$. The output of adding circuit 310 is a signal designated z(t), and this signal is coupled to a digital frame store 320 which may be of the same type as digital frame store 220 and operates in similar manner.

The output signal y(t) from subsystem 200 and the output signal z(t) from subsystem 300 are coupled to difference circuit 410 wherein the difference y(t)−z(t) is obtained. This difference signal is coupled to a digital-to-analog converter 195 (FIG. 1) for display and/or recording.

As described in the abovereferenced copending application, $k_1$ and $k_2$ can be selected to provide a desired temporal characteristic. For example, with $k_1 = 0.06$ and $k_2 = 0.006$, the composite system response peaks in the vicinity of 0.1 Hz, where much of the temporal information associated with a contrast bolus flowing through a peripheral artery would be expected to lie. The response below 0.003 Hz essentially is zero and is very small above 1 Hz.

The present invention can be utilized in conjunction with techniques which further process the series of frames generated as described herein; e.g. by the type of processing which keeps track of the maximum opacification of each pixel (as described in the copending U.S. application Ser. No. 333,558, filed Dec. 22, 1981 entitled "Method And Apparatus For Imaging A Body", assigned to the same assignee as the present application) and/or which keeps track of the time-to-maximum-opacification (as disclosed in the copending U.S. application Ser. No. 444,614 now U.S. Pat. No. 4,536,790 entitled "Apparatus And Method For Fluoroscopic Imaging Of A Body", filed of even date herewith, and also assigned to the same assignee as the present application).

The invention has been described with reference to a preferred embodiment, but variations within the spirit and scope of the invention will occur to those skilled in the art. For example, the recursive filtering system 300 can be cascaded by employing two of the described filters in series (or by passing the signals through the same filtering system twice). This serves, inter alia, to produce an overall filter characteristic that is even less responsive to the tomographic motion component.

We claim:

1. A method for generating a processed image of a cross-section through a body, comprising the steps of:
   disposing the body between a combination of a source of radiation and an associated detector, such that a beam of radiation from said source impinges angularly on said body and passes through to said detector;
   effecting relative rotational motion between said beam and said body such that a principal plane of interest in said body remains substantially in focus during said relative rotational motion;
   deriving from the detector, at different rotational positions, a series of frames of electronic video signals that represent images of the radiation transmission characteristics of the body at a series of successive times;
   temporally filtering said series of frames by combining successive frames of the series with a weighting for each combination that depends on when the frames being combined occur in time with respect to each other; and
   displaying the temporally filtered series of frames.

2. The method as defined by claim 1, further comprising the step of injecting a bolus of contrast medium into the body before deriving the frames of electronic video signals.

3. The method as defined by claim 1, wherein said temporal filtering step comprises applying said series of frames to a recursive filtering system.

4. The method as defined by claim 2, wherein said temporal filtering step comprises applying said series of frames to a recursive filtering system.

5. The method as defined by claim 2, wherein said temporal filtering step comprises filtering the series of frames of video signals with a filter function having a temporal frequency response that corresponds substantially to the temporal frequency of the movement of the bolus through the region being imaged.

6. The method as defined by claim 4, wherein said temporal filtering step comprises filtering the series of frames of video signals with a filter function having a temporal frequency response that corresponds substantially to the temporal frequency of the movement of the bolus through the region being imaged.

7. The method as defined by claim 6, wherein said recursive filtering system includes a pair of recursive filters having different temporal characteristics.

8. A method for generating a processed image of one or more cross-sections through a body, comprising the steps of:
   injecting a bolus of contrast medium into the body;
   disposing the body between a combination of a source of radiation and an associated detector, such that a beam of radiation from said source impinges angularly on said body and passes through to said detector;
   effecting relative rotational motion between said beam and said body such that a principal plane in said body remains substantially in focus during said relative potational motion;
   deriving from the detector, at different rotational positions, a series of frames of electronic video signals that represent images of the radiation transmission characteristics of the body at a series of successive times, each frame including an array of pixels, the video signal level at each pixel being determined by the radiation transmissivity of an elemental region of the principal plane and adjacent planes;
   implementing geometrical transformation to different pixel positions of video signal levels of frames of the sequence, the geometrical transformation of a pixel being a function of relative rotational angle associated with its frame, and the distance between a plane of interest to be imaged and the principal plane;
   temporally filtering the series of geometrically transformed frames; and
   displaying the temporally filtered series of geometrically transformed frames.

9. The method as defined by claim 8, wherein said temporal filtering comprises combining successive geometrically transformed frames of the series with a weighting for each combination that depends on when the frames being combined occur in time with respect to each other.

10. The method as defined by claim 8, wherein said temporal filtering step comprises applying said series of frames to a recursive filtering system.

11. The method as defined by claim 10, wherein said recursive filtering system includes a pair of recursive filters having different temporal characteristics.

12. The method as defined by claim 8, wherein said temporal filtering step comprises filtering the series of frames of video signals with a filter function having a temporal frequency response that corresponds substantially to the temporal frequency of the movement of the bolus through the region being imaged.

13. The method as defined by claim 10, wherein said step of implementing geometrical transformations to different pixel positions of video signal levels of frames of the sequence, comprises assigning modified pixel addresses to said video signal levels, and applying said modified pixel addresses to the recursive filtering system in conjunction with said video signal levels.

14. Apparatus for generating a processed image of a cross-section through a body, comprising:
   a combination of a source of radiation and an associated detector mechanically coupled together and positioned such that a beam of radiation from said source impinges angularly on said body and passes through to said detector;
   means for effecting relative rotational motion between said beam and said body such that a principal plane of interest in said body remains substantially in focus during said relative rotational motion;

means for generating from the detector output, at different rotational positions, a series of frames of electronic video signals that represent images of the radiation transmission characteristics of the body at a series of successive times;

means for temporally filtering said series of frames by combining successive frames of the series with a weighting for each combination that depends on when the frames being combined occur in time with respect to each other; and means for displaying and/or recording the temporally filtered series of frames.

15. Apparatus as defined by claim 14, wherein said temporal filtering means comprises a recursive filtering system.

16. Apparatus as defined by claim 14, wherein said temporal filtering means is operative to filter the series of frames of video signals with a filter function having a temporal frequency response that corresponds substantially to the temporal frequency of the movement of a bolus of contrast material through the region being imaged.

17. Apparatus for generating a processed image of one or more cross-sections through a body into which a bolus of contrast material has been injected, comprising:

a combination of a source of radiation and an associated detector mechanically coupled together and positioned such that a beam of radiation from said source impinges angularly on said body and passes through to said detector;

means for effecting relative rotational motion between said beam and said body such that a principal plane in said body remains substantially in focus during said relative rotational motion;

means for generating from the detector output, at different rotational positions, a series of frames of electronic video signals that represent images of the radiation transmission characteristics of the body at a series of successive times, each frame including an array of pixels, the video signal level at each pixel being determined by the radiation transmissivity of an elemental region of the principal plane and adjacent planes;

means for implementing geometrical transformation to different pixel positions of video signal levels of frames of the sequence, the geometrical transformation of a pixel being a function of relative rotational angle associated with its frame, and the distance between a plane of interest to be imaged and the principal plane;

means for temporally filtering the series of geometrically transformed frames; and means for displaying and/or recording the temporally filtered series of geometrically transformed frames.

18. Apparatus as defined by claim 17, wherein said temporal filtering means comprises a recursive filtering system.

19. Apparatus as defined by claim 17, wherein said temporal filtering means is operative to filter the series of frames of video signals with a filter function having a temporal frequency response that corresponds substantially to the temporal frequency of the movement of a bolus of contrast material through the region being imaged.

20. Apparatus as defined by claim 17, wherein said means for temporally filtering the series of geometrically transformed frames comprises means for combining successive geometrically transformed frames of the series with a weighting for each combination that depends on when the frames being combined occur in time with respect to each other.

21. A method for generating a processed image of a cross-section through a body, comprising the steps of:

injecting a bolus of contrast medium into the body;

disposing the body between a combination of a source of radiation and an associated detector, such that a beam of radiation from said source impinges angularly on said body and passes through to said detector;

effecting relative rotational motion between said beam and said body such that a principal plane of interest in said body remains substantially in focus during said relative rotational motion;

deriving from the detector, at different rotational positions, a series of frames of electronic video signals that represent images of the radiation transmission characteristics of the body at a series of successive times;

temporally filtering said series of frames with a filter function having a temporal frequency response that corresponds substantially to the temporal frequency of the movement of the bolus through the region being imaged; and displaying the temporally filtered series of frames.

22. Apparatus for generating a processed image of a cross-section through a body, comprising:

a combination of a source of radiation and an associated detector mechanically coupled together and positioned such that a beam of radiation from said source impinges angularly on said body and passes through to said detector;

means for effecting relative rotational motion between said beam and said body such that a principal plane of interest in said body remains substantially in focus during said relative rotational motion;

means for generating from the detector output, at different rotational positions, a series of frames of electronic video signals that represent images of the radiation transmission characteristics of the body at a series of successive times;

means for temporally filtering said series of frames with a filter function having a temporal frequency response that corresponds substantially to the temporal frequency of the movement of a bolus of contrast material through the region being imaged; and means for displaying and/or recording the temporally filtered series of frames.

* * * * *